United States Patent
Kempf

[19]

[11] Patent Number: 6,068,379
[45] Date of Patent: May 30, 2000

[54] DIAMOND SURFACE MIRROR

[75] Inventor: Paul S. Kempf, Encinitas, Calif.

[73] Assignee: Paul Stuart Kempf and Pilar Moreno Kempf Family Trust, Encinitas, Calif.

[21] Appl. No.: 09/312,239

[22] Filed: May 14, 1999

[51] Int. Cl.[7] .................................................. G02B 5/08
[52] U.S. Cl. ........................ 359/838; 359/882; 359/883; 359/884
[58] Field of Search .................................. 359/838, 882, 359/883, 884

[56] References Cited

U.S. PATENT DOCUMENTS

| 1,909,853 | 5/1933 | Dalton ..................................... 359/838 |
| 2,174,090 | 9/1939 | Hodny ..................................... 359/838 |
| 4,482,209 | 11/1984 | Grewal et al. ......................... 359/883 |
| 4,512,635 | 4/1985 | Melde ..................................... 359/882 |
| 5,267,090 | 11/1993 | Dowd et al. ........................... 359/844 |
| 5,428,484 | 6/1995 | Baker ..................................... 359/882 |
| 5,536,610 | 7/1996 | Ojima et al. ............................. 430/67 |
| 5,568,965 | 10/1996 | Eagan ..................................... 362/135 |

*Primary Examiner*—Cassandra Spyrou
*Assistant Examiner*—Mohammad Y. Sikder
*Attorney, Agent, or Firm*—Brown, Martin, Haller & McClain, LLP

[57] ABSTRACT

An inspection mirror incorporates an extremely thin glass substrate and low profile mount to produce a mirror that can provide visual access to spaces that would otherwise be too small or otherwise inaccessible. An aluminized layer forms the first reflecting surface. The mirror is protected by an amorphous carbon layer which forms a second reflecting surface. The mirror may be framed or frameless. Where provided, the support frame has a mirror receiving recess in which the mirror is retained by adhesive. Frameless mirrors are supported by a planar wire mount secured to the rear surface of the mirror by adhesive. The mirrors may be carried on a spring wire shaft received in a handle or by a flat strip that forms the handle and mirror support.

21 Claims, 2 Drawing Sheets

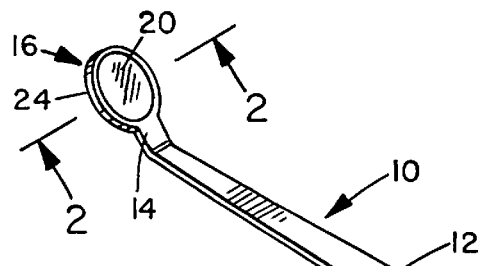
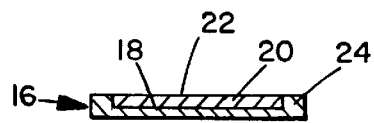
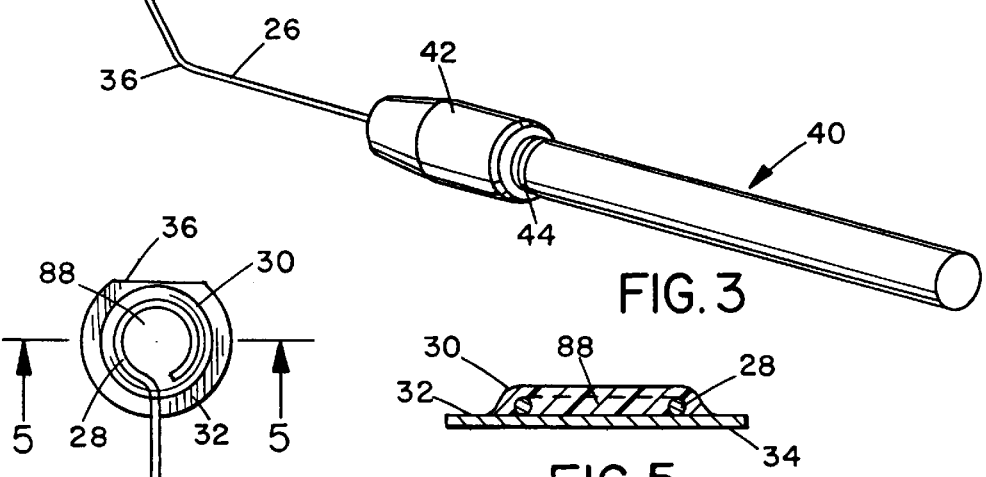
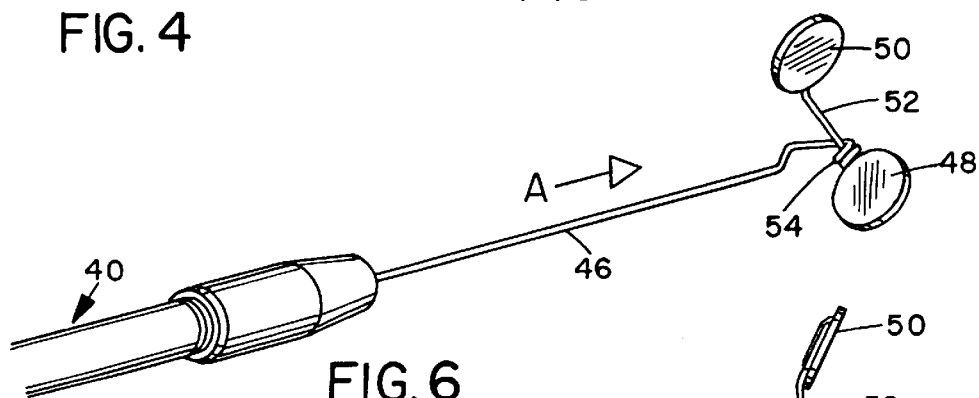
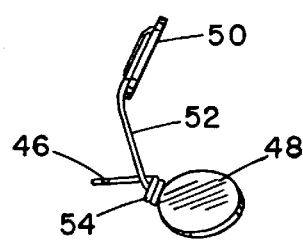

DIAMOND SURFACE MIRROR

BACKGROUND OF THE INVENTION

The present invention relates to inspection mirrors. Such mirrors are useful in inspecting printed circuit boards and like electronic components where visual access to a part or parts is restricted. Such mirrors also find application in medical settings. Dentists, in particular, use inspection mirrors to examine the teeth and to guide instruments and drill bits during procedures. A primary consideration for all inspection mirrors is the quality of the image reflected from the mirror surface. Image quality is important in direct viewing and in photography or other imaging of the surface being inspected.

The use of inspection mirrors in the inspection of printed circuit boards is described in the inventor's prior U.S. Pat. No. 4,379,647, entitled Optical Comparator and Inspection Apparatus; U.S. Pat. No. 4,938,579, Side-Viewing Mirror Device and U.S. Pat. No. 4,795,237 entitled Optical Inspection Method with Side-Viewing Mirror.

Prior art inspection mirrors have been extremely delicate and susceptible to damage. Frameless mirrors are particularly vulnerable when the substrate contacts the object under inspection. The susceptibility of prior art mirrors to damage is, in part, a result of the use of front surface metalization. Rear surface mirrors have been employed in inspection settings, but they have not proved durable either because the unprotected substrate is susceptible to damage by scratching, cracking and scoring as the mirror comes in contact with the parts under inspection. When thick substrates are employed, a degradation of the reflected image occurs.

It is therefore desirable to have an inspection mirror which provides a high-quality image while at the same time protecting the mirror from damage. Such a mirror is particularly desirable where the total thickness of the mirror and the necessary supporting structure is maintained sufficiently thin that the mirror can provide visual access to even the most restricted spaces under inspection.

SUMMARY OF THE INVENTION

In an exemplary embodiment of the invention the deficiencies of prior art inspection mirrors are overcome by providing an inspection mirror with the rear surface metalization, a support structure of minimum thickness and a protective layer for the front surface which does not interfere with, but may even enhance, the quality of the reflected image.

In a first embodiment, the mirror is positioned by the user grasping a handle connected to the mirror by a shaft. The shaft is either spring wire or small diameter cylindrical plastic. Plastic shafts are utilized where it is desired to provide direct illumination of the mirror's surface. For illumination, the shaft also performs as a light guide with the plastic material (preferably polyethylene) being directly illuminated by a battery-powered mini light or comparable light source in the handle and terminating with the axis of the shaft intersecting the plane of the mirror. Connection from the terminal end of the shaft and the mirror is accomplished by spring wire bent around the shaft and connected to the rear surface of the mirror.

In an alternative embodiment, the handle shaft and mirror support can be formed out of a single flat strip of plastic or metal which terminates in a generally planar spade end. The spade is shaped to correspond in shape with the chosen inspection mirror shape but is larger in planar dimensions than the planar dimensions of the mirror. A recess is provided in the spade surface with the exact shape of the mirror and slightly deeper than the mirror is thick. The mirror fits within the recess with only a small clearance gap around its edges.

In both embodiments, the mirror may be attached to the supporting structure utilizing adhesive. An acceptable adhesive has the characteristics that it does not shrink as it cures (which would distort the mirror and the resulting image) and which is a flowable coating at application to cover substantially all of the rear surface of the mirror and into the clearance gap on spade mount mirrors. The coating provides cushioning and protection for the mirror. For use with medical mirrors, such as dental mirrors, adhesive must also be capable of withstanding sterilization in an auto clave.

The mirrors in both embodiments are formed on a thin substrate which has a metalization layer forming a first reflecting surface and a protective layer on the front surface forming a second reflecting surface. The substrate may desirably be glass, quartz or sapphire. The protective layer is preferably amorphous carbon which is applied by exposing the front surface of the substrate to a hot plasma of carbon ions. Such coatings are sometimes referred to as diamond-like carbon or DLC. It has been found that by maintaining the substrate sufficiently thin, the spacing between the reflections from the first and second reflecting surfaces are merged by the eye or a camera into a single image. The closely spaced reflecting surfaces result in an image that has good sharpness, good reflectivity and high-resolution. Part of the enhancement of the reflected image is from a polarization effect especially, from wet or otherwise reflective surfaces which might normally produce images distorted by stray reflections. With the polarization effect achieved by the closely spaced reflecting surfaces, the surfaces instead produce an image of a higher quality even than the image that would be observed by directly viewing the surface.

BRIEF DESCRIPTION OF THE DRAWINGS

The present invention will be understood from the following detailed description of preferred embodiments of the invention taken in conjunction with the accompanying drawings in which like reference numerals refer to like parts throughout and in which:

FIG. 1 is a perspective view of one configuration of the mirror on a flat strip spade mounting;

FIG. 2 is an enlarged sectional view taken online 2—2 of FIG. 1.

FIG. 3 is a perspective view of a mirror attached to a wire frame and carried on a wire shaft which is in turn held within a chuck type handle;

FIG. 4 is an enlarged view of the mirror of FIG. 3.

FIG. 5 is an enlarged sectional view taken on the line 5—5 of FIG. 4;

FIG. 6 uses a perspective view of the dual mirror configuration;

FIG. 7 is a view taken in the direction of Arrow A in FIG. 6;

DETAILED DESCRIPTION OF THE INVENTION

Figure 8:
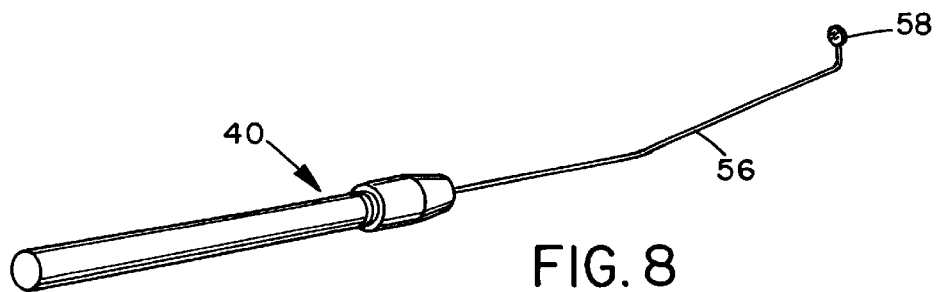
FIG. 8 is a view similar to FIG. 3, showing a very small mirror, which is made practical with practice of the present invention.

Referring to the drawings there is illustrated in FIG. 1 an embodiment of the mirror 10 according to the invention where the handle 12 is formed out of a single strip of flat plastic or metal which is inclined near the viewing end 14 to a selected viewing offset angle. The handle 12 terminates in a support spade 16 that has a recess 18 (see FIG. 2) into which the a mirror 20 is fitted and which results in a mounted mirror 20 with the front face 22 flush with the frame 24 of the spade 16. The frame 24 surrounds and protects the mirror 20. When utilized in dentistry, the handle 12 may be chucked into a special dental handle (not shown).

FIGS. 3, 4 and 5 illustrate a wire mount embodiment of the invention In this embodiment the mounting support is formed by bending a spring wire shaft 26 in a shape which defines a plane. The planar area defined is less than the area of the mounting surfaces of the mirror. The bent spring wire mount has a maximum dimension smaller than the maximum dimension of the rear surface of the mirror. The wire mounting support is referred to hereinafter as a planar wire mount 28. The mirror 34 is attached to a planar wire mount 28 by adhesive 30 which flows over and between the wire 26 to cover most of the rear surface 32 of the mirror and to protect the wire 26 from impact which would otherwise be transmitted to the rear surface 32 of the mirror. The mirror 34 illustrated incorporates an inspection flat 36 which allows the inspection mirror 34 to be placed directly against a planar surface, such as the surface of a printed circuit board, so the mirror 34 can be utilized to look under components mounted on the printed circuit board. The flexible spring wire shaft 26 is bent in two places 36 and 38 to provide clearance around obstacles and to position the handle 40 for holding at a comfortable angle and for viewing the image in the mirror. The mirror 34 lies in a plane which is displaced 90 degrees from the axis of the handle 40. Although two bends resulting in a total offset of 90 degrees are illustrated, it will be understood that virtually any combination of bends may be utilized as necessary to provide the combination of a comfortable and accessible position and angle at which to hold the handle 40, on offset of the shaft 26 to avoid obstacles, and a mirror 34 positioned to achieve the desired viewing angle. A chuck type handle 40 is incorporated. The rotatable chuck 42 is received on a threaded portion 44 of the handle 40. After the shaft 26 is inserted into the chuck 42, the chuck is rotated until the shaft 26 is held tightly. This configuration allows the mirror and shaft combination to be removed and a different configuration inserted where other viewing angles or different size mirrors are required. It also allows the shaft and mirror to be removed and be heat-sterilized, as in an auto clave.

FIGS. 6 and 7 illustrate another use of a spring wire shaft 46 and planar wire mirror support. In the illustrated configuration two complementary mirrors 48 and 50 are interconnected by a spur wire 52 which is in turn mounted by connection wraps 54 on the flexible spring wire shaft 46 and the shaft carried in a chuck type handle 40. The reflecting surfaces of the mirrors lie in intersecting planes, so that the image of one of the mirrors can be viewed by looking at the reflection in the other mirror. This allows an observer to see behind an object without having to be above the object. An example would be a dentist working on the rear surface of a molar. The use of a compound mirror has an additional advantage in that the second reflection produces an image that has true left-right orientation.

FIG. 8 shows a chuck type handle 40 with a wire shaft 56 carrying a very small round mirror 58. Mirrors as small as 0.040 inches in diameter may be produced. The ability to utilize very small mirrors is, in part, attributed to the very bright images which are achieved through the use of two reflecting surfaces. These small mirrors are also made possible by protecting the front surface from damage by utilizing a strong scratch resistant protective coating and the use of the planar wire mount.

Figure 9:
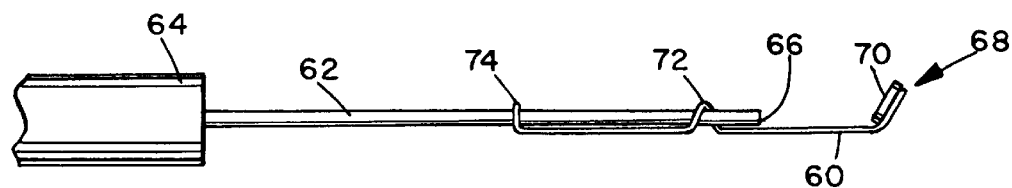
FIG. 9 is a side view of a mirror mounted on an illuminated shaft.

FIG. 9 illustrates an embodiment of the invention which combines a wire shaft 60 and a cylindrical shaft 62 in a single mirror mount. The cylindrical shaft is made of light transmitting plastic such as polyethylene. A mini light 64 forms the handle and emits a beam of light directly down the axis of the cylindrical shaft 62. The light transmitting plastic then acts as a light guide which transmits a substantial quantity of the total light to the terminus 66 of the cylindrical shaft. A mirror 68 is mounted so that the light which emits from the light guide falls on the reflecting surface 70 of the mirror and thereby illuminates the part under inspection. The wire shaft 60 is attached to the cylindrical shaft 62 by spaced wraps 72 and 74 around the cylindrical shaft 62 at spaced points to brace the wire shaft and transmit to the cylindrical shaft 62, the force generated by carrying the mirror 68 and by positioning the mirror 68 against a part under inspection.

Figure 10:
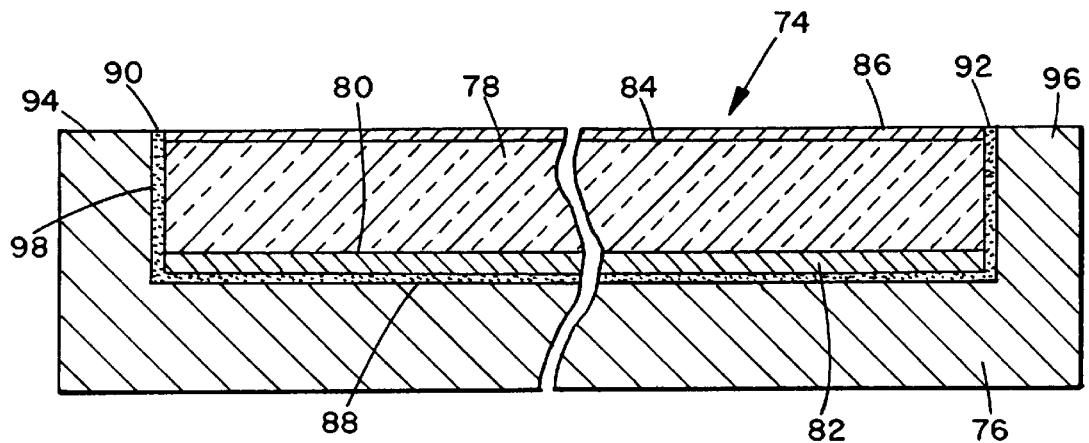
FIG. 10 is a greatly enlarged cross-section similar to FIG. 2, showing the mirror structure.

FIG. 10 illustrates the detailed structure of a mirror 74 according to the invention. The mirror 74 is shown mounted in a frame 76 which is comparable to the frame illustrated in FIG. 1. However, it will be understood that the fameless configurations of the mirror such as those illustrated in FIGS. 3 through 9, are constructed in the same manner as is the mirror 74. A thin glass substrate 78 is utilized. This substrate has a thickness of between 0.004 inches and 0.008 inches and preferably approximately 0.006 inches for use in a frame, and 0.010 inches to 0.030 inches, preferably 0.025 inches or less, when utilized frameless. The use of a very thin substrate results in closely spaced reflecting surfaces. The first reflecting surface is formed at the interface 80 between an aluminized layer and the glass substrate 78. The aluminum layer 82 is vacuum deposited to a thickness of approximately 0.0005 inches. The second reflecting surface 84 is formed at the interface between the substrate 78 and the protective coating 86. The protective coating should be harder than the objects with which the mirror's surface will come into contact and must be highly transparent. It has been found that the necessary scratch resistance for virtually all objects and the desired transparency can be achieved through the use of a diamond-like carbon layer. Therefore, the use of this material is preferred . The substrate is exposed to a plasma of carbon ions at a temperature in excess of 2000° F. After exposure time of a few seconds as determined by the selected final thickness of the DLC layer, the substrate is allowed to cool gradually which causes the carbon to coalesce into an amorphous layer. The amorphous characteristic is desirable rather than the crystalline structure associated with natural diamonds because a crystalline structure would produce reflections that would interfere with the true image. The thickness of the resulting layer is preferably less than 150 microns.

After a mirror of a selected shape is formed, the edges are polished until substantially all surface checking and cracking are removed. The polishing operation is particularly important for mirrors to be employed in frameless mounts such as the planar wire mounts. Removal of surface checking and cracking increases the amount of incidental contact which the mirror will withstand before significant chipping at the mirror edge degrades the reflected image.

The thickness of the amorphous carbon coating does not add significantly to the total thickness. Therefore, if the substrate is a nominal 0.006 inches the total thickness of the mirror will be approximately 0.007 inches or less. When mounted in a frame with a frame recess having a depth of approximately 0.008 inches, the mirror can be secured by an adhesive layer and still be flush with the top surface of the frame. It has been found that it is especially useful to apply a conformal flowable non-shrinking coating 88 into the frame recess and then use a planar tool larger in all dimensions than the mirror, to press the mirror into the recess and onto the coating. The coating then flows to cover the entire rear surface of the mirror and flows into the gaps 90 and 92 between the mirror and the side walls 94 and 96 of the recess. In this way, the peripheral edge 98 of the mirror is completely enclosed and protected against impact from parts under inspection and even from contact with the frame 76 in which the mirror 74 is mounted. A suitable coating 88 for this purpose is a silicone conformal coating such as Dow Corning coating 1-2577. This coating has the additional desirable characteristic that it will withstand exposure to auto claveing temperatures of approximately 250 degrees F. and pressures of 30 P.S.I. The same coating 88 (see FIGS. 4 and 5) may be utilized in frameless mirrors to attach the planar wire mount 28 to the rear surface of the mirror.

Although a preferred embodiment of the invention has been described above by way of example only, it will be understood by those skilled in the field that modifications may be made to the disclosed embodiment without departing from the scope of the invention, which is defined by the appended claims.

I claim:

1. An inspection mirror, comprising:

a transparent substrate having an inner side and an outer side;

a metalization layer having an inner surface and an outer surface, the inner surface being directly bonded to said inner side of said substrate;

a first reflecting surface at the interface between said metalization layer and said substrate for forming a first image on a first side of the mirror;

a protective layer having an inner surface and an outer surface, the inner surface being disposed on said outer side of said substrate forming a second reflecting surface between said protective layer and substrate, the second reflecting surface forming a second image on the first side of the mirror;

said first and second reflecting surfaces being spaced by less than 0.010 inches.

2. An inspection tool comprising:

a mirror according to claim 1 wherein:

said mirror has any selected shape and the outer surface of said metalization layer forming a mounting surface;

frame plate having a front surface substantially larger than said mirror, having a maximum thickness less than 0.020 inches, and having a recess larger than said mirror and having a minimum depth in excess of the thickness of said mirror, said recess being enclosed on at least three sides by said frame plate, said mirror being secured within said recess with the outer surface of said protective layer flush with front surface of said frame plate.

3. An inspection mirror tool comprising:

a mirror according to claim 2 wherein the mirror has any selected shape and having a mounting surface of predetermined surface area, an outer surface and having peripheral edges spaced from said mounting surface;

said peripheral edges being substantially free of surfacing cracking;

a handle;

a flexible shaft extending from said handle and terminating in a mirror attachment end;

cured adhesive connecting said attachment end of said shaft and said mounting surface of said mirror.

4. The mirror according to claim 3 wherein said peripheral edges are polished.

5. The mirror according to claim 3 wherein said adhesive is flowable when applied; does not shrink during curing, and is water insoluble.

6. The mirror according to claim 3 wherein said handle includes a source of illumination; and said flexible shaft comprises a light guide and has a first end secured to said handle for receiving light from said illumination source, said light guide transmitting light from said source in said handle to said mirror;

said mirror being supported and positioned to receive light from said light guide.

7. The mirror according to claim 1 wherein the mirror has at least one flat edge along said peripheral edge.

8. The mirror according to claim 1 wherein the thickness of said transparent substrate is approximately 0.006 inches.

9. The mirror according to claim 1 wherein said transparent substrate is glass, sapphire or quartz.

10. The mirror according to claim 1 wherein said substrate is substantially planar.

11. The mirror according to claim 1 wherein said protective layer is less than 150 microns.

12. The mirror according to claim 1 wherein said protective layer is amorphous carbon.

13. The mirror according to claim 1 wherein the maximum thickness of said frame plate is approximately 0.015 inches.

14. The device as claimed in claim 1, wherein the spacing between the first and second reflecting surfaces is less than 0.030 inches.

15. The device as claimed in claim 14, wherein the spacing is between 0.004 and 0.008 inches.

16. The device as claimed in claim 1, wherein the total thickness of the device is approximately 0.007 inches.

17. The device as claimed in claim 1, wherein the metalization layer is a vacuum deposited layer having a thickness of approximately 0.0005 inches.

18. An inspection mirror comprising:

a mirror comprising at least three layers including:

a transparent substrate;

a metalization layer on a first side of said substrate;

a first reflecting surface at the interface between said metalization layer and said substrate;

a protective layer on a second side of said substrate forming a second reflecting surface between said protective layer and substrate;

the mirror having any selected shape and having a mounting surface, an outer surface, and peripheral edges spaced from said mounting surface;

said peripheral edges being substantially free from surfacing cracking;

a handle;

a flexible shaft extending from said handle and terminating in a mirror attachment end;

cured adhesive connecting the attachment end of said shaft and said mounting surface of said mirror; and two mirrors being carried on said flexible shaft;

at least one of said mirrors being carried on a mounting spur on said shaft, and displaced from the axis of the shaft, with the reflecting surfaces of said mirrors lying on intersecting planes.

19. An inspection mirror comprising:

a mirror comprising at least three layers including:
- a transparent substrate;
- a metalization layer on a first side of said substrate;
- a first reflecting surface at the interface between said metalization layer and said substrate;
- a protective layer on a second side of said substrate forming a second reflecting surface between said protective layer and substrate;

the mirror having any selected shape and having a mounting surface having a predetermined surface area, an outer surface, and peripheral edges spaced from said mounting surface;

said peripheral edges being substantially free from surfacing cracking;

a handle;

a flexible shaft extending from said handle and terminating in a mirror attachment end;

cured adhesive connecting the attachment end of said shaft and said mounting surface of said mirror; and said mirror attachment end of said shaft is formed to define a plane and has a planar area less than the surface area of said mounting surface of said mirror.

20. An inspection mirror apparatus, comprising:

two mirrors, each mirror comprising a transparent substrate, a metalization layer on a first side of said substrate, and a first reflecting surface at the interface between said metalization layer and said substrate;

each mirror having any selected shape and having a mounting surface, an outer surface, and peripheral edges spaced from said mounting surface;

said peripheral edges being substantially free from surfacing cracking;

a handle;

a flexible shaft extending from said handle and terminating in a mirror attachment end;

cured adhesive connecting the attachment end of said shaft and said mounting surface of said mirrors; and said two mirrors being carried on said flexible shaft;

at least one of said mirrors being carried on a mounting spur on said shaft, and displaced from the axis of the shaft, with the reflecting surfaces of said mirrors lying on intersecting planes.

21. An inspection mirror, comprising:

a transparent substrate having opposite first and second sides;

a metalization layer on the first side of said substrate;

a first reflecting surface at the interface between said metalization layer and said substrate;

a protective layer on the second side of said substrate;

the mirror having any selected shape and having a mounting surface having a predetermined surface area, an outer surface, and peripheral edges spaced from said mounting surface;

said peripheral edges being substantially free from surfacing cracking;

a handle;

a flexible shaft extending from said handle and terminating in a mirror attachment end;

cured adhesive connecting the attachment end of said shaft and said mounting surface of said mirror; and said mirror attachment end of said shaft is formed to define a plane and has a planar area less than the surface area of said mounting surface of said mirror.

* * * * *

UNITED STATES PATENT AND TRADEMARK OFFICE
CERTIFICATE OF CORRECTION

PATENT NO. : 6,068,379　　　　　　　　　　　　　　　　　　　　　Page 1 of 1
DATED　　　 : May 30, 2000
INVENTOR(S) : Paul S. Kempf It is certified that error appears in the above-identified patent and that said Letters Patent is hereby corrected as shown below:

<u>Claim 2, column 5,</u>
Line 61, after "protective layer" please insert -- substantially -- therein.

Signed and Sealed this

Eighteenth Day of September, 2001

*Attest:*

*Attesting Officer*　　　　　NICHOLAS P. GODICI
　　　　　　　　　　　　*Acting Director of the United States Patent and Trademark Office*